United States Patent [19]

Somor

[11] Patent Number: 4,838,875
[45] Date of Patent: Jun. 13, 1989

[54] METHOD AND APPARATUS FOR DEALING WITH INTRAVENOUS FLUIDS

[76] Inventor: Andrew T. Somor, 2430 N. Parkside, Chicago, Ill. 60639

[21] Appl. No.: 130,442

[22] Filed: Dec. 9, 1987

[51] Int. Cl.[4] .............................................. A61M 5/00
[52] U.S. Cl. .................................... 604/262; 604/247; 604/408
[58] Field of Search ........ 604/262, 247, 256, 408–410, 604/416, 323, 81.92; 383/44

[56]  References Cited

U.S. PATENT DOCUMENTS

| | | |
|---|---|---|
| 3,159,176 | 12/1964 | Russell et al. . |
| 3,207,372 | 9/1965 | Evans . |
| 3,465,784 | 9/1969 | Cofoid . |
| 3,568,977 | 1/1969 | Nelson . |
| 3,648,697 | 3/1972 | Gardner . |
| 4,030,495 | 6/1977 | Virag . |
| 4,084,606 | 4/1978 | Mittleman . |
| 4,114,617 | 9/1978 | Turner et al. . |
| 4,141,379 | 2/1979 | Manske . |
| 4,186,740 | 2/1980 | Guerra . |
| 4,222,407 | 9/1980 | Ruschke et al. . |
| 4,244,379 | 1/1981 | Smith . |
| 4,303,067 | 12/1981 | Connolly et al. ................... 604/408 |
| 4,310,017 | 1/1982 | Raines . |
| 4,324,238 | 4/1982 | Genese et al. . |
| 4,391,598 | 7/1983 | Thompson . |
| 4,405,316 | 9/1983 | Mittleman . |
| 4,411,652 | 10/1983 | Kramer et al. . |
| 4,426,024 | 1/1984 | Hogan et al. . |
| 4,430,074 | 2/1984 | Mooring . |
| 4,447,230 | 5/1984 | Gula et al. . |
| 4,535,820 | 8/1985 | Raines . |
| 4,556,086 | 8/1985 | Raines . |
| 4,658,655 | 4/1987 | Kanno . |
| 4,683,916 | 8/1987 | Raines ................................... 604/247 |
| 4,687,474 | 8/1987 | Takanashi ........................... 604/258 |

Primary Examiner—Stephen C. Pellegrino
Attorney, Agent, or Firm—Irwin C. Alter

[57] ABSTRACT

An apparatus is disclosed for intravenous administration of fluid to which fluid may be added according to the process also disclosed, by injecting same, using a syringe, but not a needle, directly into the hollow portion of the apparatus through an opening therein. A normally closed backflow check valve device, having a component thereof acting as a means for receiving the fluid by engagement to the syringe, has been permanently sealed into the opening in the hollow portion of the apparatus. The apparatus is capped by a double luer locking cap, the purpose of which is to protect the opening into the apparatus from contamination. This is accomplished by using a cap structure wherein the cap which will ultimately re-cover the opening is locked into and protected by the cap which initially covers the opening and then discarding this initial cap after the apparatus has been filled.

13 Claims, 1 Drawing Sheet

METHOD AND APPARATUS FOR DEALING WITH INTRAVENOUS FLUIDS

BACKGROUND OF THE INVENTION

This invention discloses an intravenous apparatus and a procedure for filling same which employs a normally closed backflow check valve device, a syringe, and anti-contamination caps of luer lock design. While none of these articles is novel, in itself, to the art of intravenous fluid administration, this particular combination of elements, put to the particular purpose described herein, is totally new and constitutes a substantial improvement over prior art.

Basically, my invention constitutes improvements in pharmaceutical apparatus and procedure. In a hospital pharmacy, it is regularly necessary to add fluids to intravenous containers which may or may not already contain other fluid or fluid soluble material. For example, containers of a base liquid, such as blood, might require infusion with an anti-coagulant, or an antibiotic might be added to containers already containing sterile water or a nutrient feeding solution such as dextrose. For a situation which would involve the addition of fluid to an intravenous container which held fluid-soluble dry material, see Gardner, U.S. Pat. No. 3,648,697. (See later discussion of this patent under Prior Art.)

Since there is no reason for the intravenous container to be pre-filled with any substance before my invention may be utilized to advantage, it should be realized that this procedure and apparatus may be used by a blood bank or other distributing or manufacturing site to fill intravenous containers initially.

DISCUSSION OF PRIOR ART

The use of a backflow check (backcheck or reflux) valve is far from new in the field of intravenous administration apparatus and in the equipment used in conjunction therewith. Such known arrangements are shown in Mittleman, U.S. Pat. Nos. 4,084,606 and 4,405,316, Turner et al., U.S. Pat. No. 4,114,617, and Gula et al., U.S. Pat. No. 4,447,230. The last three patents listed focus on the patient, with the accomplishment being, basically, a simultaneous or serial administration of more than one parenteral fluid to him through the same apparatus. The first Mittleman U.S. Pat. No. 4,084,606, also involves multiple sources of fluid, but the focus is on the transfer within the administration system from a first reservoir to a second reservoir, and ultimately on the flow of these combined or sequential injections into the system's outlet.

The present invention, on the other hand, focuses on the filling with or admixture of fluids into the intravenous container itself, not with the subtleties and complexities of the tubing and connections emanating therefrom to the patient or to other containers. The one patent which truly is relevant is Raines, U.S. Pat. No. 4,683,916. This is the precise type of backflow check valve which my invention preferably utilizes.

Somewhat relevant to my own invention is another device which, like my own invention, is concerned generally with the filling of an intravenous reservoir with fluid. The device is Hogan et al., U.S. Pat. No. 4,426,024. However, whereas the reservoir or intravenous container itself, with its backcheck valve fill-component, is the focus of my invention, Hogan et al.'s device, A DEVICE FOR DISPENSING FLUIDS, is just what its name implies; it is, basically, a syringe activator. Thus, far from creating an issue of obviousness or non-novelty over the prior art, the device disclosed in U.S. Pat. No. 4,426,024 is complementary to my own.

Finally, there is Gardner's invention, U.S. Pat. No. 3,648,697. While the focus of the Gardner invention is the intravenous container, and the filling thereof with fluid through an opening, the purpose and operation of our two inventions are very remote. The Gardner intravenous container has only one opening, which is the "discharge" or outlet opening. Using a needle, fluid is injected into this opening, which is stopped by a rubber-like material adapted to be pierced by the needle. The Gardner device does include a check valve, but it consists simply of a ball, which seats itself above the opening when the fluid has drained out. Thus, the purpose of this rudimentary valve device is quite different from the one sealed into my own device. The Gardner ball seats itself in the container's neck, forming a seal on the container's outlet so that air cannot flow our from the empty container into a patient's veins. The purpose of the Raines-type backflow check valve in my device is to prevent backflow of fluid which has been added to the container, using the valve device itself as a conduit for this fluid. Another dissimilarity between the Gardner device and my own device is an element of mine totally lacking in the Gardner device, namely, the cap over the fluid receptacle which protects it and the contents of the intravenous container from contamination.

While this discussion of relevant prior art is, of course, necessary to any patent disclosure, the precise nature of my own invention is perhaps lost in the discussion because, finally, my own apparatus is so different from, and such an improvement over, any of these other devices or combinations thereof, that its novelty and usefulness can best be seen by a brief, affirmative summary of the actual device, rather than a recitation of what it is not.

SUMMARY OF THE INVENTION

The present invention comprises an apparatus for intravenous administration of fluids and a process for transferring fluids into same wherein a backflow check valve device, including a syringe engagement component, has been permanently sealed into an opening in the apparatus. This opening comes supplied with a luer lock cap which protects it from contamination.

It is an object of this invention to provide an apparatus for intravenous administration of fluid which may have fluid added to it through a normally closed backflow check valve integral to the apparatus.

It is another object of this invention to have a non-invasive procedure for filling an intravenous container with fluid through the use of a syringe only, with no needle, wherein the syringe engages directly with a normally closed backflow check valve.

It is yet another object of this invention to provide an apparatus for intravenous administration of fluid which, because of the lack of need for transfer needles, obviates the common problem of puncturing the side walls of the plastic bag comprising said apparatus and also obviates the resultant mess and loss of expensive solution caused by such a puncture.

It is further an object of this invention to provide an apparatus for intravenous administration of fluid which, by virtue of eliminating the need for transfer needles in the use of said apparatus, creates a substantial cost savings.

It is still further an object of this invention to provide an apparatus for intravenous administration of fluid which has an anti-contamination capping device connected thereto which consists of a double luer locking cap which may be removed and unlocked and re-applied in such a way that the cap still protects the opening of the apparatus from contamination from the exterior environment.

It is still further an object of this invention to provide an apparatus for intravenous administration of fluid wherein a handle for hanging the apparatus is integral with the hollow, fluid-containing component of said apparatus.

Other and further objects, advantages and features of my invention will become more readily apparent in the following description, wherein a preferred embodiment of the invention is described, especially when read in conjunction with the accompanying drawings, wherein:

DETAILED DESCRIPTION OF THE PREFERRED EMBODIMENT

Figure 1:
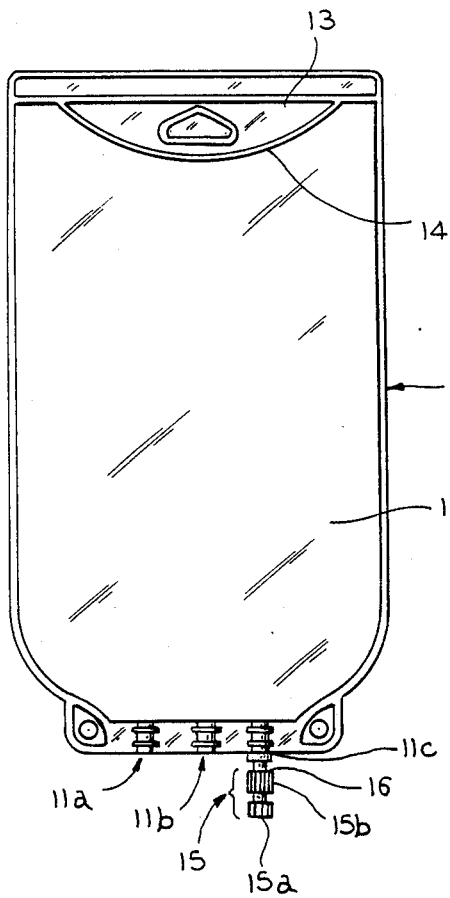
FIG. 1 is an elevational view, not to scale, of the assembled device of the present invention.

Referring generally to the figures in the drawings, wherein like parts are indicated by corresponding numerals throughout the several views, FIG. 1 consists of a plastic intravenous container 10 containing three openings 11a, 11b and 11c leading into the hollow fluid-containing portion 12 of the container 10. The container is depicted as empty in these drawings. A handle 13 is integral with the hollow fluid-containing portion of the container 12 and is sealed off therefrom by fusion 14 of the two halves of the container.

A double luer locking cap structure 15, in which the two component caps 15a and 15b are serially connected to each other, is locked into a female taper 16. This taper also serves as a syringe engagement component of the backflow check valve device 17 shwon cross-sectionally in FIG. 2, and which is sealed into the opening 11c of the intravenous container.

Figure 2:
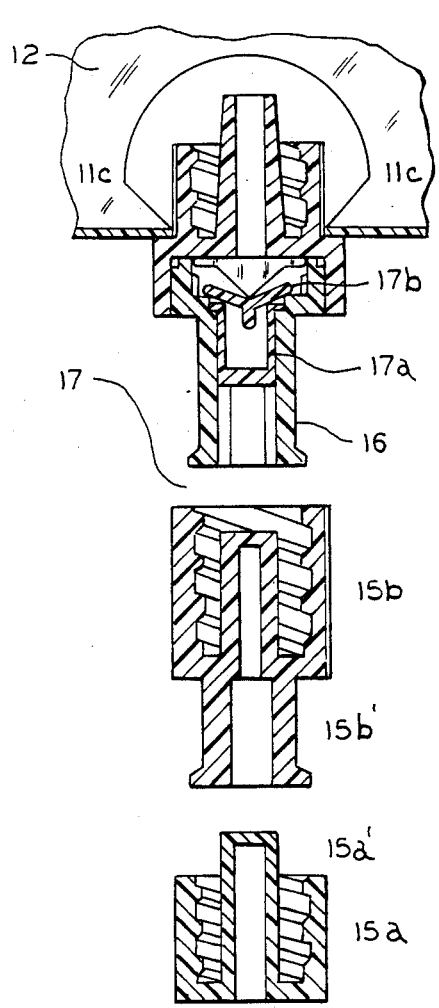
FIG. 2 is an exploded, cross-sectional view of the double cap structure and backflow check valve device taken along 2-2 of FIG. 3.

FIG. 2 shows, cross-sectionally, another component 17a of the backflow check valve device, consisting of a ring with legs extending therefrom which is concentrically received in the female taper 16. This ring component 17a is made to slide within said taper 16 by the force of fluid (not shown) being injected from a syringe 18 (see FIG. 4) through the syringe tip 19 into the valve device 17 sealed into opening 11c into the hollow portion 12 of the intravenous container. As seen from the drawings, the syringe 18 is an example of a non-invasive fluid feeding device. Also shown cross-sectionally in FIG. 2, is the flexible valve disk 17b in its normally closed position.

Figure 3:
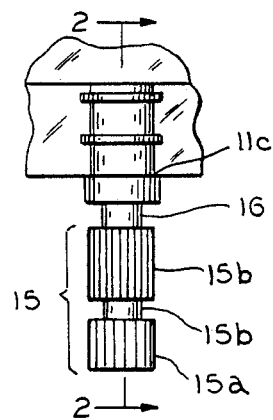
FIG. 3 is a front elevational view, slightly enlarged from actual size, of the components of FIG. 2 in their assembled state.

FIG. 3 shows the two caps 15a and 15b serially locked together as a unit 15 wherein the distal cap 15a is fashioned with a male taper luer lock connector 15a' which fits into and locks securely with the female taper luer lock connector 15b' extending from the cap 15b which is proximal to the intravenous container. The male taper 15a', being totally enclosed by the female taper 15b' of the proximate cap 15b, is protected from contamination from the exterior environment.

Figure 4:
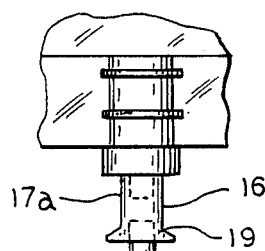
FIG. 4 is a schematic view of the syringe being inserted into the backflow check valve device.

FIG. 4 shows the double cap structure having been removed and in its place a syringe 18, whose tip 19 (shown in phantom) is fashioned in the manner of a compatible male taper luer locking connector, is locked into the female taper component 16 of the valve device 17. Fluid (not shown) is then injected from the syringe 18 through the valve device 17 forcing the movable means or ring component 17a (shown in phantom) to move in the direction of the flexible valve disk 17b (not shown in FIG. 4), opening the valve, and flowing into the hollow portion 12 of the intravenous container. The valve disk 17b returns to its closed position and the syringe tip 19 may be unlocked and the syringe withdrawn.

The double capping structure which has been removed as a unit may now be separated into its component parts 15a and 15b and the cap 15b, which had formerly been locked into the female taper component 16 of the valve device 17 may now be discarded.

Figure 5:
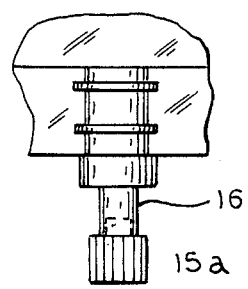
FIG. 5 shows a syringe engagement component of the backflow check valve device covered with the outer cap of the double cap structure.

FIG. 5 shows cap 15a alone, used to re-cover the syringe engagement component 16 of the valve device.

From the preceding description it becomes apparent that an improved and cost-saving apparatus for the intravenous administration of fluids and an improved process for filling same have been described. Through the use of a normally closed backflow check valve, a syringe, and a double capping structure, fluids may be safely and conveniently added to an intravenous container without the need for transfer needles.

The caps are removed as a unit so that the outer cap is still protected from external contamination; the syringe tip is locked into the compatible, fluid feeding component of the backflow check valve; the desired amount of fluid is non-invasively fed through the syringe into the opening of the apparatus, activating the valve; the syringe is unlocked and withdrawn, reseating the valve; the two caps are separated; and the non-contaminated outer cap is locked over the opening of the apparatus.

It is, of course, understood that the description herein is by way of illustration, rather than limitation. Changes, modifications and various applications of this invention may be made without departing from the spirit and the scope of the invention, especially as defined by the scope of the claims appended hereto.

Having thus described my invention, what I claim and desire to secure by Letters Patent in the United States is:

1. An apparatus for intravenous administration of fluid wherein some fluid may or may not be already contained in a hollow portion of said apparatus, and the apparatus is fed with fluid through at least one opening therein, a normally closed backflow check valve securely received in said opening in fluid-tight fashion, said valve including as a component, a valve member, a receptacle for the introduction of fluid therethrough, a movable means within the receptacle, said receptacle having a first removable cap associated therewith, whereby removal of said cap can enable a non-invasive fluid feeding device to be associated with said receptacle to feed fluid into said apparatus, whereby the valve member is forced away from its sealed, flow-preventing position by movable means contacting against said valve member in response to the forceful introduction of fluid from this device, whereafter the feeding device is removed, the valve member returns to its seated position, and the first cap is replaced on the receptacle.

2. An apparatus as described in claim 1 wherein the fluid feeding device is a syringe.

3. An apparatus as described in claim 1 wherein the fluid receptacle is a standardized female taper luer lock mating connector, and the cap is constructed in the manner of a male mate to this fluid receptacle.

4. An apparatus as described in claim 3 whereby when the cap is secured to the fluid receptacle, the exterior of said receptacle is protected from contamination from the exterior environment.

5. An apparatus as described in claim 3 wherein the fluid receptacle is associated with a second cap to form a double capped structure whereby the two caps are serially connected with each other and both may be removed as a unit.

6. An apparatus as described in claim 5 wherein the serial connection of the caps, one to the other, is such that the cap which is proximal to the female luer lock fluid receptacle and locked therewith by virtue of a standard male luer lock connector at the proximal end, has a distal end constructed in the manner of a standardized female luer lock connector whereby it receives and locks with the distal cap, and whereby, because of these standardized connections, the two-cap unit may be further separated into its two component caps, and the distal cap may, by itself, be used to securely lock the fluid receptacle on said apparatus, and whereby the male connecting end of said distal cap is protected from contamination from the exterior environment as long as it remains connected to the proximal cap.

7. An apparatus as described in claim 1 wherein a handle for hanging the apparatus is integral therewith.

8. An apparatus as described in claim 1 wherein it includes an additional opening in said apparatus through which fluid contained in a hollow portion of the apparatus may flow out.

9. An apparatus as described in claim 1 wherein the fluid-tight fastening is by means of a threaded inlet port and a complementarily threaded valve body.

10. A process for the transfer of biological fluid from an external source into an apparatus for intravenous administration of fluid, wherein there is employed a flexible plastic container including a hollow portion, at least one opening leading into said hollow portion, a normally closed backflow check valve device received in said opening, said valve device including, as a component, a receptacle for the introduction of fluids therethrough, which receptacle can accept fluid by engagement with a non-invasive fluid feeding device, a removable cap associated with said receptacle, and a non-invasive fluid feeding device, and wherein the steps comprise:

(a) securely fastening, in a fluid-tight manner, the normally closed backflow check valve device into the opening of the intravenous container;

(b) covering the opening of said valve device with the cap structure and locking same into said valve device;

(c) filling the fluid feeding device with the fluid to be transferred into the intravenous container;

(d) removing the cap structure from the intravenous container;

(e) locking the fluid feeding device into the fluid receptacle component of the valve device;

(f) injecting a desired amount of fluid from the fluid feeding device through the check valve, non-invasively, into the opening of the intravenous container;

(g) unlocking and withdrawing the fluid feeding device; and (h) re-covering the opening of said valve device.

11. A process as described in claim 10 wherein the fluid feeding device is a syringe, and the cap structure consists of two caps locked to each other by means of standardized male and female luer lock connectors whereby the cap distal from the intravenous container opening, the male, is connected to the distal (female) end of the proximal cap in the same manner as the proximal cap is locked over the opening of the valve device, and whereby the syringe-engaging fluid receptacle component of said valve device is protected from contamination from the exterior environment.

12. A process as described in claim 10 wherein the double cap structure is removed from the intravenous container and wherein the two component caps are kept as a single unit, with the distal cap remaining locked to the proximal cap, and whereafter the caps are unlocked from each other, and the proximal cap, which had been locked into the syringe engagement component of the valve device, is discarded.

13. A process as described in claim 10 wherein the formerly distal cap alone is used to re-cover the end of the syringe engagement component of the valve device.

* * * * *